United States Patent
Manford et al.

(10) Patent No.: US 11,219,602 B2
(45) Date of Patent: Jan. 11, 2022

(54) METHOD FOR MAKING A MICRONIZED DRY POWDER FORMULATION OF GLYCOPYRROLATE AND MAGNESIUM STEARATE

(71) Applicant: VECTURA LIMITED, Wiltshire (GB)

(72) Inventors: Fergus Paul Manford, Wiltshire (GB); Matthew Green, Wiltshire (GB)

(73) Assignee: VECTURA LIMITED, Wiltshire (GB)

( * ) Notice: Subject to any disclaimer, the term of this patent is extended or adjusted under 35 U.S.C. 154(b) by 0 days.

(21) Appl. No.: 16/493,866

(22) PCT Filed: Mar. 14, 2018

(86) PCT No.: PCT/EP2018/056456
§ 371 (c)(1),
(2) Date: Sep. 13, 2019

(87) PCT Pub. No.: WO2018/167180
PCT Pub. Date: Sep. 20, 2018

(65) Prior Publication Data
US 2020/0078302 A1 Mar. 12, 2020

(30) Foreign Application Priority Data
Mar. 15, 2017 (EP) .................................... 17161214

(51) Int. Cl.
*C07D 207/12* (2006.01)
*A61K 9/14* (2006.01)
*A61K 9/00* (2006.01)
*A61K 31/40* (2006.01)
*A61K 31/4704* (2006.01)
*A61K 31/573* (2006.01)

(52) U.S. Cl.
CPC ............ *A61K 9/145* (2013.01); *A61K 9/0075* (2013.01); *A61K 31/40* (2013.01); *A61K 31/4704* (2013.01); *A61K 31/573* (2013.01)

(58) Field of Classification Search
CPC .................................................... C07D 207/12
USPC ......................................................... 548/541
See application file for complete search history.

(56) References Cited

FOREIGN PATENT DOCUMENTS

| WO | 200032165 | 6/2000 |
|---|---|---|
| WO | 2005105043 | 11/2005 |
| WO | 2008000482 | 1/2008 |
| WO | 2012120284 | 9/2012 |
| WO | 2016038116 | 3/2016 |

*Primary Examiner* — Douglas M Willis
(74) *Attorney, Agent, or Firm* — Barnes & Thornburg LLP; Ryan P. Cox (57) ABSTRACT

Methods are disclosed for simultaneously jet milling and conditioning particulate glycopyrrolate and magnesium stearate using a milling gas having humidity between 5% and 30% Relative Humidity in the grinding chamber of a jet mill, the jet mill is configured with a humidifier arranged to supply humidity into the grinding chamber. A composition and formulation comprising physically stable micronized composite glycopyrrolate particles made by this method is also disclosed.

19 Claims, 5 Drawing Sheets

METHOD FOR MAKING A MICRONIZED DRY POWDER FORMULATION OF GLYCOPYRROLATE AND MAGNESIUM STEARATE

CROSS-REFERENCE TO RELATED APPLICATIONS

This application is a United States national stage of International Application No. PCT/EP2018/056456, filed Mar. 14, 2018, which was published as International Publication No. WO 2018/167180, and which claims benefit of European Application No. 17161214.6, filed Mar. 15, 2017, the entire contents of each of which are hereby expressly incorporated herein by reference.

INTRODUCTION

This application relates to methods used for the preparation of stabilized particulate glycopyrrolate, preferably to methods and systems which imparts physicochemical stability to particulate glycopyrrolate as well as compositions incorporating such particles.

BACKGROUND

Crystalline particulate glycopyrrolate as supplied by active pharmaceutical ingredient (API) manufacturers is generally too big to be used in respiratory formulations and often requires size reduction (micronisation). Typically, unmicronised crystalline particulate glycopyrrolate will exist in particle sizes substantially greater than 10 μm, with typical distributions resembling $D_{10}$>10 μm, $D_{50}$>90 μm, $D_{90}$>250 μm. One method of micronizing particulate glycopyrrolate is jet milling.

The multiple high speed/high energy collisions that occur within the grinding chamber of a jet mill provide the milling action which is required to break the glycopyrrolate particles down to the appropriate size. This process, however, can result in particle characteristics with an undesired level of physiochemical instability. It is also well known that such milling action may induce the generation of non-crystalline (amorphous) material, especially on the surface of the glycopyrrolate particles where particles have collided either with each other or the side of the grinding chamber of the jet mill. Such non-crystalline material can lead to significant physicochemical instability of the resulting micronized glycopyrrolate particles resulting in glycopyrrolate particles that may fuse, aggregate, and/or agglomerate. Amorphous material may be present in the form of amorphous regions on an otherwise crystalline glycopyrrolate particle.

It has been suggested that conducting a post micronisation conditioning step in the presence of moisture may help to reduce the generation of amorphous material on the glycopyrrolate particle. These processes, however, are inconvenient and can be lengthy and labour intensive.

There remains a need for an improved method for micronizing glycopyrrolate particles that preserves their physical stability whilst removing the need for inconvenient, lengthy and labour intensive post micronisation conditioning procedures.

SUMMARY OF THE INVENTION

We disclose an improved process involving co-jet milling glycopyrrolate and magnesium stearate with a milling gas having humidity between 5% and 30% Relative Humidity in the grinding chamber of the jet mill to produce physically stable micronized composite particles as determined by Dynamic Vapour Sorption (DVS) along with imparting an excellent Particle Size Distribution (PSD) profile determined by laser diffraction as measured by $D_{10}$, $D_{50}$ and $D_{90}$ values.

Unlike the prior art which uses post micronisation conditioning, the method of the invention supplies humidity directly into the grinding chamber thereby avoiding the need for inconvenient, lengthy and labour intensive post micronisation conditioning procedures that are required to remove amorphous material.

Furthermore, supplying humidity directly into the grinding chamber during micronisation of the glycopyrrolate allows for real time modification of the processing parameters and in particular a reduction in the generation of amorphous material. This removes the need for the micronized powders to be set aside for post micronisation conditioning before then combining with, for example, carrier particles.

The method of the invention also allows additional components to be used in the solution from the provided humidity. These additional components may be introduced into the grinding chamber at the point of micronisation which avoids contaminating the pressurised gas lines leading to the jet mill.

DETAILED DESCRIPTION OF INVENTION

Systems and methods for simultaneously milling and conditioning particulate glycopyrrolate in a jet mill are described herein involving a method of making a dry powder formulation, the method comprising jet milling particles of glycopyrrolate in an amount of from 50% (w/w) to 99.9% (w/w) and magnesium stearate in an amount of from 0.1% (w/w) to 50% (w/w) of the combined glycopyrrolate and magnesium stearate, using a milling gas having humidity between 5% and 30% Relative Humidity in the grinding chamber of the jet mill to produce physically stable micronized composite particles.

In one embodiment methods for simultaneously milling and conditioning particulate glycopyrrolate in a jet mill is disclosed, wherein the milling gas humidity is between 6% and 29% Relative Humidity, preferably between 10% and 29% Relative Humidity, preferably between 15% and 29% Relative Humidity, preferably between 20% and 29% Relative Humidity, preferably between 21% and 29% Relative Humidity, as measured by a hygrometer.

In one embodiment methods for simultaneously milling and conditioning particulate glycopyrrolate in a jet mill is disclosed, wherein the method comprises jet milling particles of glycopyrrolate in an amount of from 55% (w/w) to 99.9% (w/w) and magnesium stearate in an amount of from 0.1% (w/w) to 45% (w/w) of the combined glycopyrrolate and magnesium stearate.

In one embodiment methods for simultaneously milling and conditioning particulate glycopyrrolate in a jet mill is disclosed, the method comprising jet milling particles of glycopyrrolate in an amount of from 60% (w/w) to 99.9% (w/w) and magnesium stearate in an amount of from 0.1% (w/w) 40% (w/w) of the combined glycopyrrolate and magnesium stearate.

In one embodiment methods for simultaneously milling and conditioning particulate glycopyrrolate in a jet mill is disclosed, the method comprising jet milling particles of glycopyrrolate in an amount of from 65% (w/w) to 99.9%

(w/w) and magnesium stearate in an amount of from 0.1% (w/w) to 35% (w/w) of the combined glycopyrrolate and magnesium stearate.

In one embodiment methods for simultaneously milling and conditioning particulate glycopyrrolate in a jet mill is disclosed, the method comprising jet milling particles of glycopyrrolate in an amount of from 70% (w/w) to 99.9% (w/w) and magnesium stearate in an amount of from 0.1% (w/w) to 30% (w/w) of the combined glycopyrrolate and magnesium stearate.

In one embodiment methods for simultaneously milling and conditioning particulate glycopyrrolate in a jet mill is disclosed, the method comprising jet milling particles of glycopyrrolate in an amount of from 75% (w/w) to 99.9% (w/w) and magnesium stearate in an amount of from 0.1% (w/w) to 25% (w/w) of the combined glycopyrrolate and magnesium stearate.

In one embodiment methods for simultaneously milling and conditioning particulate glycopyrrolate in a jet mill is disclosed, the method comprising jet milling particles of glycopyrrolate in an amount of from 80% (w/w) to 99.9% (w/w) and magnesium stearate in an amount of from 0.1% (w/w) to 20% (w/w) of the combined glycopyrrolate and magnesium stearate.

In one embodiment methods for simultaneously milling and conditioning particulate glycopyrrolate in a jet mill is disclosed, the method comprising jet milling particles of glycopyrrolate in an amount of from 85% (w/w) to 99.9% (w/w) and magnesium stearate in an amount of from 0.1% (w/w) to 15% (w/w) of the combined glycopyrrolate and magnesium stearate.

In one embodiment methods for simultaneously milling and conditioning particulate glycopyrrolate in a jet mill is disclosed, the method comprising jet milling particles of glycopyrrolate in an amount of from 90% (w/w) to 99.9% (w/w) and magnesium stearate in an amount of from 0.1% (w/w) to 10% (w/w) of the combined glycopyrrolate and magnesium stearate.

In one embodiment methods for simultaneously milling and conditioning particulate glycopyrrolate in a jet mill is disclosed, the method comprising jet milling particles of glycopyrrolate in an amount of from 95% (w/w) to 99.9% (w/w) and magnesium stearate in an amount of from 0.1% (w/w) to 5% (w/w) of the combined glycopyrrolate and magnesium stearate.

In one embodiment methods for simultaneously milling and conditioning particulate glycopyrrolate in a jet mill is disclosed, the method comprising jet milling particles of glycopyrrolate in an amount of from 97.5% (w/w) to 99.9% (w/w) and magnesium stearate in an amount of from 0.1% (w/w) to 2.5% (w/w) of the combined glycopyrrolate and magnesium stearate.

In one embodiment methods for simultaneously milling and conditioning particulate glycopyrrolate in a jet mill is disclosed, the method comprising jet milling particles of glycopyrrolate in an amount of from 99% (w/w) to 99.9% (w/w) and magnesium stearate in an amount of from 0.1% (w/w) to 1% (w/w) of the combined glycopyrrolate and magnesium stearate.

In one embodiment methods for simultaneously milling and conditioning particulate glycopyrrolate in a jet mill is disclosed, wherein the humidity in the milling gas is supplied by a humidifier arranged to supply moisture to the jet mill grinding chamber.

In one embodiment methods for simultaneously milling and conditioning particulate glycopyrrolate in a jet mill is disclosed, wherein the humidity in the milling gas is supplied by an aerosol generator arranged to supply liquid aerosol to the jet mill grinding chamber.

In one embodiment methods for simultaneously milling and conditioning particulate glycopyrrolate in a jet mill is disclosed, wherein the aerosol generator is external to the jet mill grinding chamber and the external aerosol generator is configured with a port to supply liquid aerosol into the jet mill grinding chamber.

In one embodiment methods for simultaneously milling and conditioning particulate glycopyrrolate in a jet mill is disclosed, wherein a port is arranged to simultaneously supply particles of glycopyrrolate, magnesium stearate and liquid aerosol as a feed stock into the grinding chamber of the jet mill.

In one embodiment methods for simultaneously milling and conditioning particulate glycopyrrolate in a jet mill is disclosed, wherein a port is arranged to simultaneously supply a co-located particles of glycopyrrolate, magnesium stearate and liquid aerosol as a feed stock into the grinding chamber of the jet mill.

In one embodiment methods for simultaneously milling and conditioning particulate glycopyrrolate in a jet mill is disclosed, wherein a aerosol generator produces liquid aerosol with a $D_{90}$ less 100 µm, preferably less 50 µm or more preferably less 20 µm prior to entering the grinding chamber of the jet mill as measured by laser diffraction.

In one embodiment methods for simultaneously milling and conditioning particulate glycopyrrolate in a jet mill is disclosed, the method further comprising blending the composite glycopyrrolate particles with particles of excipient carrier, preferably wherein the excipient carrier is lactose, more preferably anhydrous lactose, more preferably alpha-lactose monohydrate.

In one embodiment, a formulation is disclosed comprising co-jet milled particles of glycopyrrolate and magnesium stearate obtained or obtainable by the methods described herein.

In one preferred embodiment, the magnesium stearate forms a coating on the surface of the glycopyrrolate particles as measured by energy-dispersive X-ray spectroscopy.

In one embodiment a dry powder inhaler is disclosed, containing a formulation comprising co-jet milled micronized composite particles of glycopyrrolate and magnesium stearate, made according to the methods described herein.

In one embodiment, a method of treating a respiratory disease is disclosed, the method comprising administering to a patient co-jet milled micronized composite particles of glycopyrrolate and magnesium stearate, made according to the methods described herein.

In one embodiment, use of co-jet milled micronized composite particles of glycopyrrolate and magnesium stearate, made according to the methods described herein, for the treatment of a respiratory disease is disclosed, preferably wherein the respiratory disease is chronic obstructive pulmonary disease (COPD), asthma, cystic fibrosis (CF) and related airway diseases is disclosed.

In one embodiment, a pharmaceutical kit is disclosed, the kit comprising co-jet milled micronized composite particles of glycopyrrolate and magnesium stearate, made according to the methods described herein, the micronized composite particles being in combined or separate unit dosage forms, said forms being suitable for administration of the composite glycopyrrolate and magnesium stearate and, optionally a further active in effective amounts, optionally together with one or more inhalation devices for administration of the actives.

In one embodiment methods for simultaneously milling and conditioning particulate glycopyrrolate in a jet mill is disclosed, wherein the physically stability of the micronized composite glycopyrrolate particles is determined by particle size analysis.

In one embodiment, the methods described herein involve a jet mill wherein the jet mill is a spiral jet mill, a fluidized bed jet mill, an opposed fluid jet mill or a high density bed jet mill.

In one embodiment, the methods described herein involve a jet mill wherein the aerosol generator comprises a nebuliser, preferably wherein the nebuliser is a vibrating mesh, jet nebulizer or an ultrasonic wave nebulizer.

In one embodiment, the methods described herein involve a jet mill wherein the aerosol generator produces a condensed vapour.

In one embodiment, the methods described herein involve a jet mill wherein the aerosol generator comprises a spray drying atomiser, a two-fluid nozzle atomiser or a centrifugal atomiser.

In one embodiment, the methods described herein involve a jet mill further comprising a powder feeder wherein the powder feeder comprises a rotary valve, a vibratory tray or a screw feeder, preferably wherein the powder feed rates ranges from 10 g/hour to production mill rates of up to 900 kg/hr.

In one embodiment, the methods described herein involve a jet mill, wherein the aerosol generator produces liquid aerosol which has a temperature less than 100° C. upon entering the grinding chamber.

In one embodiment, the methods described herein involve a jet mill wherein the aerosol generator produces a liquid aerosol at atmospheric pressure.

In one embodiment, the methods described herein involve a jet mill wherein the liquid aerosol is combined with particles of glycopyrrolate and magnesium stearate at atmospheric pressure.

In one embodiment, the methods described herein involve a jet mill comprising a vortex modifier for altering the residence times of a feed stock in the grinding chamber, wherein the feed stock comprises a grinding material and liquid aerosol, preferably wherein the grinding material is glycopyrrolate and magnesium stearate.

In one embodiment, the methods described herein involve a process of producing stable micronized composite particles, the method comprising jet milling a feed stock comprising particles of glycopyrrolate and liquid aerosol.

In one embodiment, the methods described herein involve a process wherein the grinding material comprises particles of glycopyrrolate and magnesium stearate, optionally unmicronised particulate material.

In one embodiment, the methods described herein involve a process wherein the grinding material comprises particles of glycopyrrolate and magnesium stearate and an additional pharmaceutical additive.

In one embodiment, the methods described herein involve a process wherein the additional pharmaceutical additive is in an amount of from 1 to 25% (w/w), more preferably from 2 to 20% (w/w), more preferably 3 to 15% (w/w), more preferably 4 to 10% (w/w) but most preferably from 5 to 7.5% (w/w) of the co-jet milled combination of the pharmaceutically active material (i.e. the glycopyrrolate) and pharmaceutical excipient.

In one embodiment, the methods described herein involve a process wherein the additional pharmaceutical additive is selected from a metal stearate, sodium lauryl sulphate, sodium stearyl fumarate, sodium stearyl lactylate, preferably calcium stearate, lithium stearate, sodium stearate, zinc stearate, stearyl alcohol or sodium benzoate.

In one embodiment, the methods described herein involve a process wherein the grinding material comprises particles of glycopyrrolate and magnesium stearate, and further comprises a pharmaceutical excipient.

In one embodiment, the methods described herein involve a process wherein the pharmaceutical excipient carrier particles comprise lactose, mannitol, glucose, trehalose, cellobiose, sorbitol or maltitol.

In one embodiment, the methods described herein involve a process wherein milling gas humidity is produced at atmospheric pressure.

In one embodiment, the methods described herein involve a process wherein the liquid aerosol is produced at atmospheric pressure.

In one embodiment, the methods described herein involve a process wherein the milling gas humidity is combined with the grinding material at atmospheric pressure.

In one embodiment, the methods described herein involve a process wherein the liquid aerosol is combined with the grinding material at atmospheric pressure.

In one embodiment, the methods described herein involve a process wherein the jet mill uses a milling gas selected from air, hydrogen, helium, nitrogen, carbon dioxide or combination thereof.

In one embodiment, the methods described herein involve a process wherein the liquid aerosol comprises a pharmaceutically active material.

In one embodiment, the methods described herein involve a process wherein the liquid aerosol comprises a pharmaceutical additive.

In one embodiment, the methods described herein involve a process wherein the liquid aerosol comprises a pharmaceutical excipient.

In one embodiment, the methods described herein involve a process wherein the milling step occurs at a temperature in the range from 5° C. to 50° C., preferably 10° C. to 40° C., more preferably 15° C. to 30° C.

In one embodiment, the methods described herein involve a process wherein the jet milling is carried out at an averaged powder feed rate of between 0.1 and 50 g/min, preferably at a feed rate of between 0.5 and 40 g/min, preferably at a feed rate of between 1 and 30 g/min, preferably at a feed rate of between 1.5 and 25 g/min, preferably at a feed rate of between 0.1 and 20 g/min, preferably at a feed rate of between 0.5 and 15 g/min, preferably at a feed rate of between 1 and 10 g/min, preferably at a feed rate of between 1.5 and 5 g/min.

In one embodiment, the methods described herein involve a process wherein the jet milling is carried out at a grinding pressure of more than 2 bar below an inlet pressure.

In one embodiment, the methods described herein involve a process wherein the jet milling is carried out at an inlet pressure of between 3 and 12 bar, preferably at an inlet pressure of between 4 and 10 bar, or more preferably at an inlet pressure of between 5 and 9 bar.

In one embodiment, the methods described herein involve a process wherein the grinding pressure is carried out at between 1 and 10 bar, preferably at a pressure of between 2 and 8 bar, or more preferably at a pressure of between 3 and 7 bar.

In one embodiment, the methods described herein involve a process for reducing the presence of amorphous material on the surface of a micronized glycopyrrolate comprising combining the glycopyrrolate, magnesium stearate and liquid aerosol as a feed stock in a grinding chamber and jet milling the feed stock.

In one embodiment, the methods described herein involve a process wherein a further pharmaceutically active material is selected from indacaterol and/or mometasone.

In one embodiment, the methods described herein involve a process wherein the micronized glycopyrrolate particles contain less than 5% (w/w), less than 4% (w/w), less than 3% (w/w), less than 2% (w/w), preferably less than 1% (w/w) amorphous material immediately after milling as measured by dynamic vapour sorption.

In one embodiment, a formulation made by a method is described, wherein the micronized glycopyrrolate particles contain less than 5% (w/w), less than 4% (w/w), less than 3% (w/w), less than 2% (w/w), preferably less than 1% (w/w) amorphous material immediately after milling as measured by dynamic vapour sorption.

In one embodiment, the methods described herein involve jet milling particulate material with a liquid aerosol, the liquid aerosol being at least a partial solvent of the glycopyrrolate.

In one embodiment a formulation is disclosed, made by a method described herein, for use in treatment of a respiratory condition, wherein the respiratory condition is any of chronic obstructive pulmonary disease (COPD), asthma, cystic fibrosis (CF) or related airway diseases.

Description of the Jet Mill

The method of the invention is not limited to the illustrated embodiments.

The improved method comprises a jet milling apparatus in which a feed stock, comprising particles of glycopyrrolate and magnesium stearate and liquid aerosol, is entrained in a flow of gas causing the entrained particles of glycopyrrolate and magnesium stearate to repeatedly collide and cause size reduction of the particles of glycopyrrolate and magnesium stearate to produce physically stable micronized composite particles. A circulating gas flow, such as the described vortex below, increases the interaction length for collisions between the particles of glycopyrrolate and magnesium stearate. The feed stock, comprising particles of glycopyrrolate and magnesium stearate and liquid aerosol, need not be entrained in a separate gas flow and could be introduced under gravity into the milling chamber.

Figure 1:
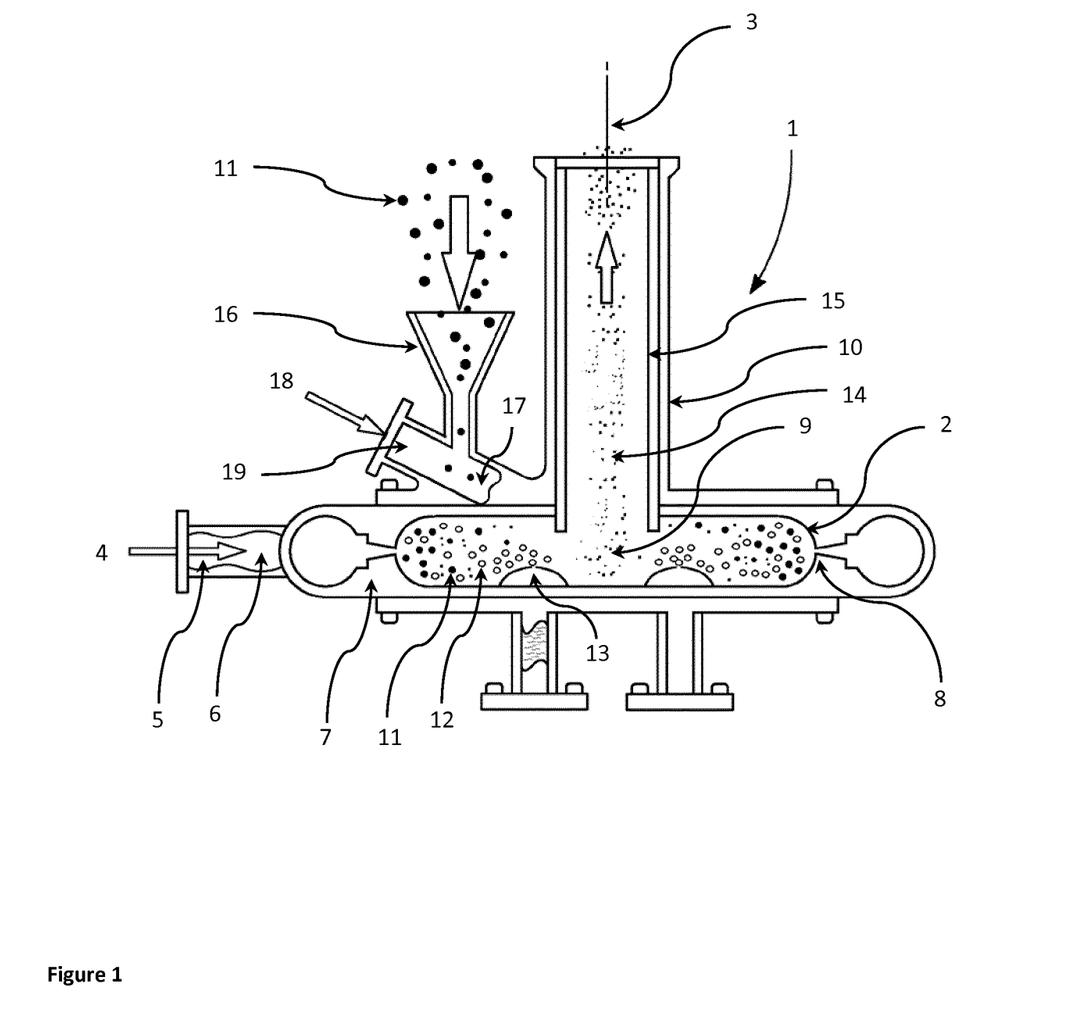
FIG. 1 is a partially sectioned view of a jet mill with an internal aerosol generator arranged to supply liquid aerosol into the grinding chamber of the jet mill.
Figure 2:
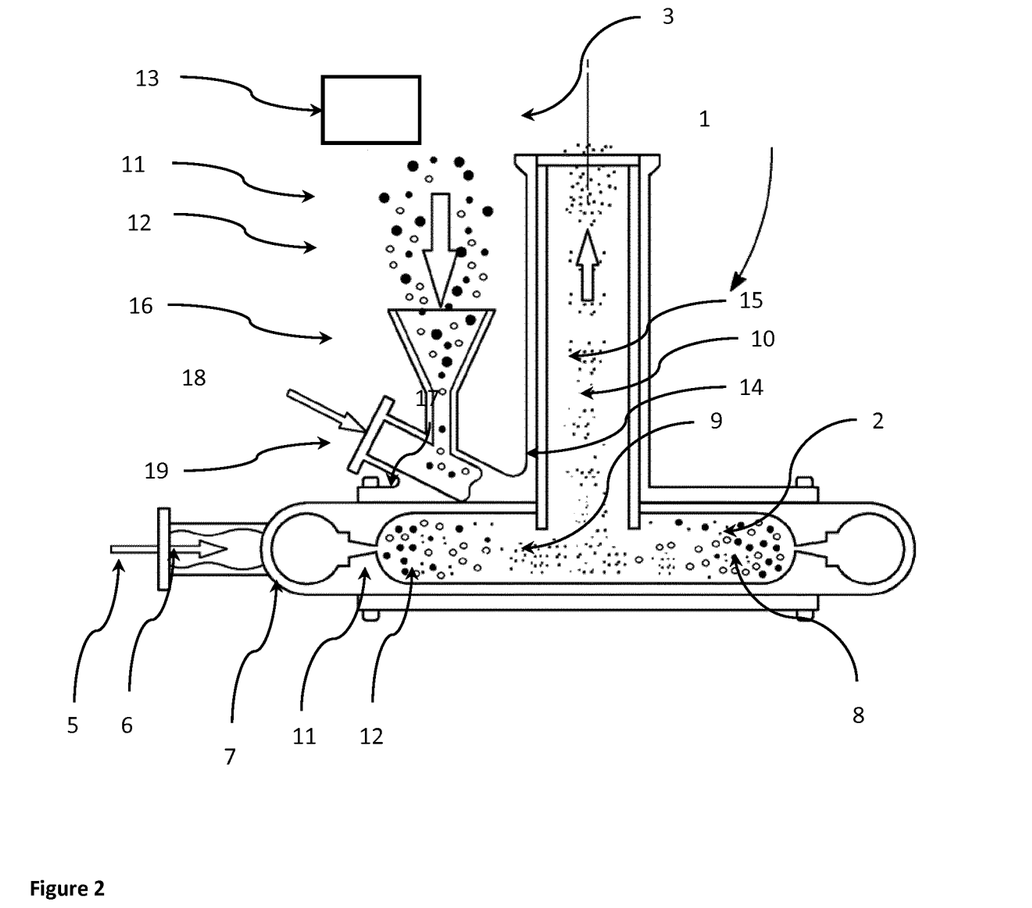
FIG. 2 is a partially sectioned view of a jet mill with an external aerosol generator arranged to supply liquid aerosol into the grinding chamber of the jet mill.
Figure 3:
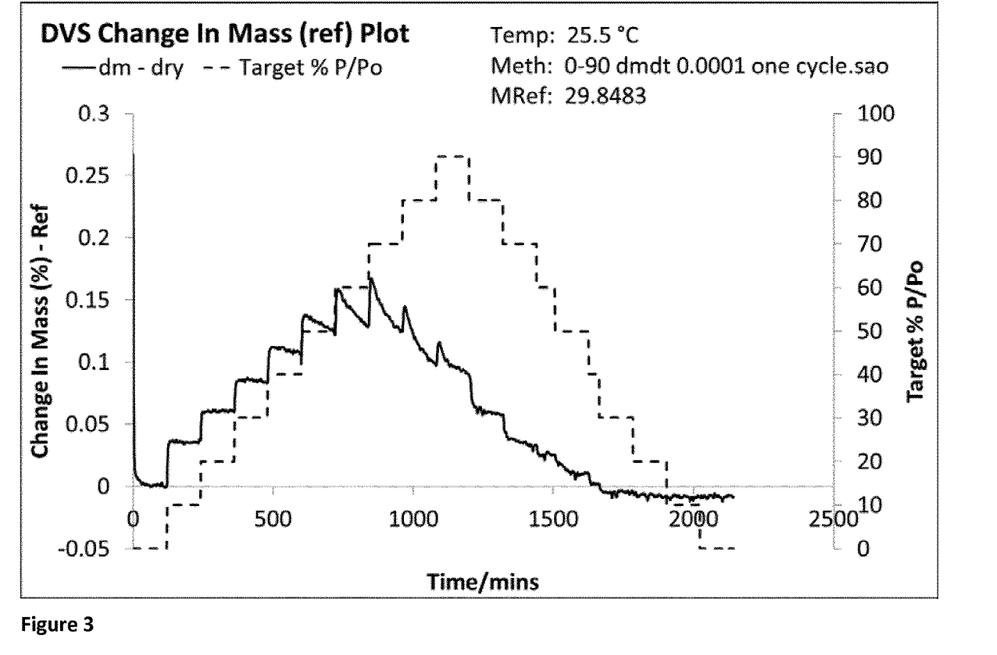
FIG. 3 shows the DVS trace for jet milled glycopyrrolate only using a milling gas having humidity 2.8-3.5% RH and then analysed by DVS immediately after micronisation.

A jet mill 1 to be used in the method of the invention is illustrated in the partially sectioned view of FIG. 1 or FIG. 2.

A substantially cylindrical milling chamber 2 is arranged around a central axis 3 extending vertically in the illustrated embodiment.

Compressed mill gas 4 is supplied through a gas intake 5 to a gas manifold 6 between the mill body 7 and the milling chamber 2. A plurality of jet holes 8 transfer the compressed mill gas 4 into the outer periphery of the milling chamber 2. The jet holes 8 are all aligned to set up a circulating gas flow pattern, in particular a vortex 9 of the mill gas 4 and other gas within the milling chamber 2. That is, the jet holes 8 are tangentially aligned to introduce compressed mill gas 4 into the milling chamber 2 to create a vortex 9 gas flow pattern. The resulting vortex 9 forms an inwardly directed spiral flow beginning near the outer periphery of the milling chamber 2 about the central axis 3 and shrinking with continuously decreasing radius until it is close to the central axis 3 and an outlet 10 arranged around the central axis 3 on one axial side of the milling chamber 2. The outlet 10, which forms an extraction hole for the vortex gases and entrained micronized particles, extends away from the milling chamber 2 along the chamber central axis 3.

The gas in the milling chamber 2 and any entrained particles of glycopyrrolate and magnesium stearate 11 are combined with liquid aerosol 12 provided by an aerosol generator 13 arranged to supply liquid aerosol 12 into the grinding chamber 2.

In one configuration, a plurality of aerosol generators 13 may be arranged within the grinding chamber 2. In one configuration, the aerosol generator 13 may be positioned towards the periphery of the milling chamber 2. In one configuration, the aerosol generator 13 may be positioned towards the central axis 3 of the milling chamber 2.

In one configuration, the multiple aerosol generators 13 may supply different liquids presented as different liquid aerosols 12 into the grinding chamber 2.

In one configuration, the grinding chamber 2 envelopes an aerosol generator 13 arranged to supply liquid aerosol 12 into the grinding chamber 2.

In another configuration, an aerosol generator 13 is configured to supply liquid aerosol 12 and particles of glycopyrrolate and magnesium stearate 11 into the grinding chamber 2.

The gas in the vortex 9 and any entrained particles of glycopyrrolate and magnesium stearate 14 are exhausted through the outlet pipe 10 away from the milling chamber 2 for collection in a suitable device such a collection bag or suitable cyclone apparatus.

In one configuration, a vortex modifier is placed adjacent to the vortex 9 within the grinding chamber 2. This configuration permits modification of the residence times of the entrained particles of glycopyrrolate and magnesium stearate 14 and liquid aerosol 12 within the grinding chamber 2 thereby extending the contact of the liquid aerosol 12 with the particles of glycopyrrolate and magnesium stearate 14, depending on the nature of the specific drug and jet milling parameters to be used.

In one configuration, a slidable vortex modifier 15 fits with the outlet pipe 10 and is moveable along the outlet pipe 10 so that the bottom of the slidable vortex modifier 15 can be placed at a selected axial position adjacent to the vortex 9 within the grinding chamber 2. This configuration permits modification of the residence times of the entrained particles of glycopyrrolate and magnesium stearate 14 and liquid aerosol 12 within the grinding chamber 2 thereby extending the contact of the liquid aerosol 12 with the particles of glycopyrrolate and magnesium stearate 14, depending on the nature of the specific drug and jet milling parameters to be used.

Particles of glycopyrrolate and magnesium stearate 11 are loaded into a feed funnel 16 to feed the particles of glycopyrrolate and magnesium stearate 11 into a port 17, for example a feed tube. The port is tangentially aligned to introduce particles of glycopyrrolate and magnesium stearate 11 into the milling chamber 2 in the direction of the vortex 9 gas flow pattern. Compressed feed gas 18 is supplied to a feed gas inlet 19 directing the feed gas 18 toward the particles of glycopyrrolate and magnesium stearate 11 falling with them through the funnel 16. The feed gas 18 entrains the particles of glycopyrrolate and magnesium stearate 11 and flows into the milling chamber 2.

The port 17 may be formed in a side wall of the mill body 7 to introduce particles of glycopyrrolate and magnesium stearate 11 at the outer periphery of the milling chamber 2 in the direction of the vortex 9 gas flow pattern.

In another configuration, the port 17 is arranged to simultaneously supply a grinding material, for example particles of glycopyrrolate and magnesium stearate 11 and liquid aerosol 12 as a feed stock into the grinding chamber 2.

The swirling vortex 9 accelerates the particles of glycopyrrolate and magnesium stearate 11 into a generally circular path within the milling chamber 2. The pulverization of the material primarily occurs from particle-to-particle impact although some particles of glycopyrrolate and magnesium stearate 11 impact against the walls of the milling chamber 2. The tangential velocity of the vortex 9 generally increases towards the chamber central axis 3. Centrifugal force drives the larger particles towards the perimeter of the milling chamber 2, while finer particles are swept by the vortex 9 and move towards the chamber central axis 3, eventually exiting the milling chamber 2 through the outlet 10 together with the two gases 4 and 18.

The milling gas 4 and feed gas 18 should preferably be clean and all the connective piping and contact surfaces within the jet mill should preferably be made of stainless steel, ceramic or polymer preferably with polished gas-facing surfaces.

The jet mills used in the method according to the invention typically involves the supply of gas, such as nitrogen, helium or air at pressures in the region of about 4 to 14 bar, typically 6 to 12 bar and the particles to be milled are entrained in the feed gas. High-purity nitrogen typically supplied from a liquid-nitrogen tank or clean air is advantageously used for both the milling 4 gas and feed gas 18.

The jet milling operation is typically conducted at standard pressure occurs at close to atmospheric pressure, and has a milling duration measured in milliseconds.

The final outlet temperature of the jet milling is typically at about room temperature (preferably between 10° C. and 35° C., more preferably between 20° C. and 26° C.). Typically, the milling gas is introduced into the mill at about room temperature, and exits the mill at about the same temperature. During the process however, the gas will change temperature significantly as it exits the supersonic nozzle (lower pressure and temperature) and is subsequently warmed by the energy released in the jet milling operation. Preferably the jet milling temperature is above 0° C.

The temperature of the liquid aerosol may also be controlled prior to and upon entering the grinding chamber of the jet mill. Immediately following fracture in the grinding chamber in the presence of the liquid aerosol, the surfaces of the particles of glycopyrrolate immediately undergo a process of amorphous to crystalline reversion rather than experience a delay before this annealing can occur when processed downstream of the jet mill. This amorphous to crystalline reversion process can be significantly affected by the temperature of the liquid aerosol in the grinding chamber. In certain embodiments, the temperature of the liquid aerosol in the grinding chamber is less than 100° C. In specific embodiments, the temperature of the liquid aerosol in the grinding chamber may be selected from one of the following ranges, between about 1° C. and 80° C., between about 5° C. and 50° C., between about 10° C. and 40° C., and between about 15° C. and 35° C., preferably between about 20° C. and 30° C. or preferably between about 22° C. and 28° C., depending on the nature of the particulate material being processed.

In a specific embodiment the liquid aerosol solution permits the use of a liquid aerosol at or below 0° C. Salts such as pharmaceutically active materials will create freezing point depression. In specific embodiments, the temperature of the liquid aerosol in the grinding chamber may be selected from one of the following ranges, between about −20° C. and 100° C., between about −15° C. and 90° C., between about −10° C. and 80° C., between about −5° C. and 35° C. or between about −1° C. and 30° C.

The invention allows the inexpensive production of stable micronized glycopyrrolate particles with a narrow PSD. Furthermore, a jet mill used in the method according to the invention can be retrofitted with few parts on existing commercially available equipment.

Pharmaceutically Active Material

In one aspect, the method according to the invention comprises glycopyrrolate formulated with indacaterol maleate, preferably for use in simultaneous or sequential administration in the treatment of an inflammatory or obstructive airways disease, optionally wherein any single formulation, or any combined formulation, comprises at least one particulate pharmaceutically acceptable carrier.

In one aspect, the method according to the invention comprises glycopyrrolate formulated with indacaterol maleate and mometasone furoate, preferably for use in simultaneous or sequential administration in the treatment of an inflammatory or obstructive airways disease, optionally wherein any single formulation, or any combined formulation, comprises at least one particulate pharmaceutically acceptable carrier.

In a preferred method, glycopyrrolate is formulated in combination with indacaterol maleate and mometasone furoate wherein the glycopyrrolate has been co-jet milled with magnesium stearate using a milling gas having humidity between 5% and 30% Relative Humidity.

Co-Jet Milling

The terms "co-micronise" and "co-jet mill" are synonymous when used herein and refer to the micronisation process achieved when particles are micronised and/or coated in the grinding chamber of a jet mill.

Preferably glycopyrrolate particles and magnesium stearate are pre-mixed to give a roughly homogeneous blend before being co-jet milled together as measured as a percentage coefficient of variation, as known in the art, of less than 25%, preferably less than 20%, more preferably less than 15%.

Co-jet milling glycopyrrolate particles and magnesium stearate, further reduces the propensity of the glycopyrrolate particles to form >10 µm aggregates/agglomerates immediately after milling. When co-jet milled, magnesium stearate particles form a physically fused and proud particulate coating on the drug particles, and they create inter-particulate spaces between the drug particles. The presence of this coating can be established by energy-dispersive X-ray spectroscopy (EDX). The presence of composite particles can be determined by aerosolising a sample from an inhaler into a Next Generation Impactor (NGI) at 60 L/min (equivalent to a 4 kPa pressure drop). Double coated carbon conductive tabs are placed directly under the air nozzles of stages 5, 6 and 7 of the NGI to capture the smaller powder particles. Double coated adhesive tabs prevent movement of the tab during the NGI assessment but are also small enough so that the overall airflow characteristics of the NGI pathway are not adversely affected. Once done, the powder-coated carbon conductive tabs can be transferred to SEM carbon specimen mounts, or similar. The sample can be viewed using SEM and EDX specifically looking for co-location of an atom that is unique to the additive and a separate atom unique to the drug particle, for example magnesium in the case of magnesium stearate and bromine in the case of glycopyrronium bromide.

In a preferred embodiment glycopyrrolate particles and magnesium stearate are jet milled in a Hosokawa Alpine® 100 AFG fluid bed opposed jet mill. Other suitable jet milling equipment include, for example, the MC 44 IR Chrispro® Jet-Mill or MC50, MC100, MC200, MC300 (Micromacinazione SA), Hosokawa's Alpine® AS-50, AS-100, AFG 140, AFG200, AFG280 and AFG400 jet mills.

The co-jet milling powder feed rates for a 50 mm diameter jet mill, for example a Hosokowa AS-50, should be kept low (preferably <20 g/min) to ensure an optimal coating of the glycopyrrolate particles material by the magnesium stearate. Feed rates higher than 20 g/min still achieve coating by the magnesium stearate but it will be sub-optimal because too much powder passes through the mill to ensure sufficient energy is applied to each particle to achieve the desired coating with magnesium stearate. Feed rates will vary depending on the size of the mill used. Consequently, jet mills with 100 mm diameters, for example a Hosokowa AS-100 spiral jet mill, will be able to accommodate higher feed rates, typically <50 g/min. The jet milling may be carried out at an averaged powder feed rate of preferably between 0.1 and 50 g/min, preferably at a feed rate of between 0.5 and 40 g/min, preferably between 1 and 30 g/min, preferably between 1.5 and 25 g/min, preferably between 0.1 and 20 g/min, preferably between 0.5 and 15 g/min, preferably between 1 and 10 g/min, preferably between 1.5 and 5 g/min.

Where necessary or useful, the glycopyrrolate particles and/or magnesium stearate are sieved prior to co-jet milling.

Pharmaceutical Excipients

In a yet further method according to the invention, the feed stock comprises a pharmaceutical excipient. Dry powder formulations for inhalation in the treatment of respiratory diseases are generally formulated by mixing a micronised active pharmaceutical ingredient with coarse carrier particles to give an ordered mixture. The carrier particles make the micronised active pharmaceutical ingredient less cohesive and improve its flowability. This makes the powder easier to handle during the manufacturing process. The micronised active particles tend to adhere to the surface of the carrier particles when stored in a dry powder inhaler device but are dispersed from the surfaces of the carrier particles on inhalation into the respiratory tract to give a fine aerosol. The larger carrier particles impact on the throat due to their inertia and are mostly deposited in the oropharyngeal cavity.

One embodiment may include carrier particles which are mixed with the glycopyrrolate particles and magnesium stearate that has been jet milled with liquid aerosol in a ratio of from 2000:1 to 5:1 by mass, especially from 200:1 to 20:1 by mass. The carrier particles may be composed of any pharmacologically inert material or combination of materials which is acceptable for inhalation. They are suitably composed of one or more crystalline sugars including monosaccharides, disaccharides, polysaccharides and sugar alcohols such as arabinose, glucose, fructose, ribose, mannose, sucrose, trehalose, lactose, maltose, starches, dextran, mannitol or sorbitol. An especially preferred carrier is lactose, for example lactose monohydrate or alpha lactose monohydrate or anhydrous lactose.

Preferably substantially all (by weight or volume) of the carrier particles have a diameter of 20 to 1000 µm, more preferably 50 to 500 µm, but especially 20 to 250 µm. The diameter of substantially all (by weight) of the carrier particles is suitably less than 355 µm. This provides good flow and entrainment characteristics and improved release of the active particles in the airways to increase deposition of the active particles in the lower lung.

It will be understood that throughout this specification the diameter of the particles referred to is the diameter of the particles as suitably determined by a Malvern Mastersizer or similar laser diffraction equipment.

Ambient Conditions

"Ambient conditions" as used herein are defined as 22° C.±5° C. and 40-50% RH. The terms "ambient temperature" and "ambient humidity" as used herein are defined as 22° C.±5° C. and 40-50% RH respectively.

EXAMPLES

Selected embodiments of the present invention will now be explained with reference to the examples. It will be apparent to those skilled in the art from this disclosure that the following descriptions of the embodiments are for illustration only and not for the purpose of limiting the invention as defined by the appended claims and their equivalents.

The examples below illustrate how co-jet milled glycopyrrolate and magnesium stearate particles may be prepared using a milling gas having humidity between 5% and 30% Relative Humidity which simultaneously reduces the size of the primary particles whilst also removing surface non-crystalline material present, thereby removing the need for a sequential post micronisation conditioning step.

Particle Size Analysis (Wet Analysis)

The particle size distribution for the micronized glycopyrrolate formulations was determined by Malvern Mastersizer 3000 using the Hydro MV wet dispersion unit as follows: the dispersion unit was filled with iso-octane (2,2,4-trimethylpentane). The pump speed was set to 3000 rpm. Ten millilitres of 0.1% lecithin in iso-octane was added to approximately 10 mg of the micronized glycopyrrolate formulation, this pre-dispersion was then sonicated for 3 minutes using a Sonopuls sonic probe at 50% intensity. The dispersed particles were added to the dispersion unit to reach an obscuration of 5-15%. The optical properties used included a refractive index of 1.52 and an absorption value of 1.0 for the glycopyrrolate, and a refractive index of 1.45 and an absorption value of 1.0 for the magnesium stearate and a refractive index of 1.391 for the iso-octane. Six replicates were performed per measurement.

Dynamic Vapour Sorption

The amorphous content for micronized glycopyrrolate was assessed by DVS using an SMS DVS Advantage instrument which was set to a temperature of 25° C. The humidity was increased from 0-90% RH then returned to 0% RH in steps of 10% RH, changes between steps which were triggered by a mass change of 0.0001 (% dm/dt).

Example 1: Co-Jet Milled Glycopyrrolate and Magnesium Stearate (1% w/w) in Humidified Gas (25% RH) Using Liquid Aerosol Unmicronised glycopyrrolate ($D_{10}$=2.89 µm, $D_{50}$=16.0 µm, $D_{90}$=49.0 µm determined by Malvern Mastersizer 3000 wet analysis method) was pre-stirred with magnesium stearate ($D_{10}$=2.8 µm, $D_{50}$=8.8 µm, $D_{90}$=27.4 µm determined by Malvern Mastersizer 3000 wet analysis method) in a glass beaker using a metal spatula for 30 seconds before micronization in an AS-50 spiral jet mill (Inlet pressure=5 Bar, Grinding Pressure=3 Bar, Averaged Feed Rate=2 g/min).

The Formulation was produced by using a milling gas at elevated humidity (22.9-24.6% RH and at 18.4-18.6° C.) using liquid aerosol. The outlet of an ultrasonic wave nebuliser was connected to the grinding chamber of an AS-50 jet mill via tube piping ensuring that water did not drip into the grinding chamber and that nebulised water aerosol combined with the unmicronised glycopyrrolate and magnesium stearate. The humidities were measured prior to jet milling by placing a portable hygrometer with the probe in the exiting gas stream at the outlet of the collection vessel.

Figure 4:
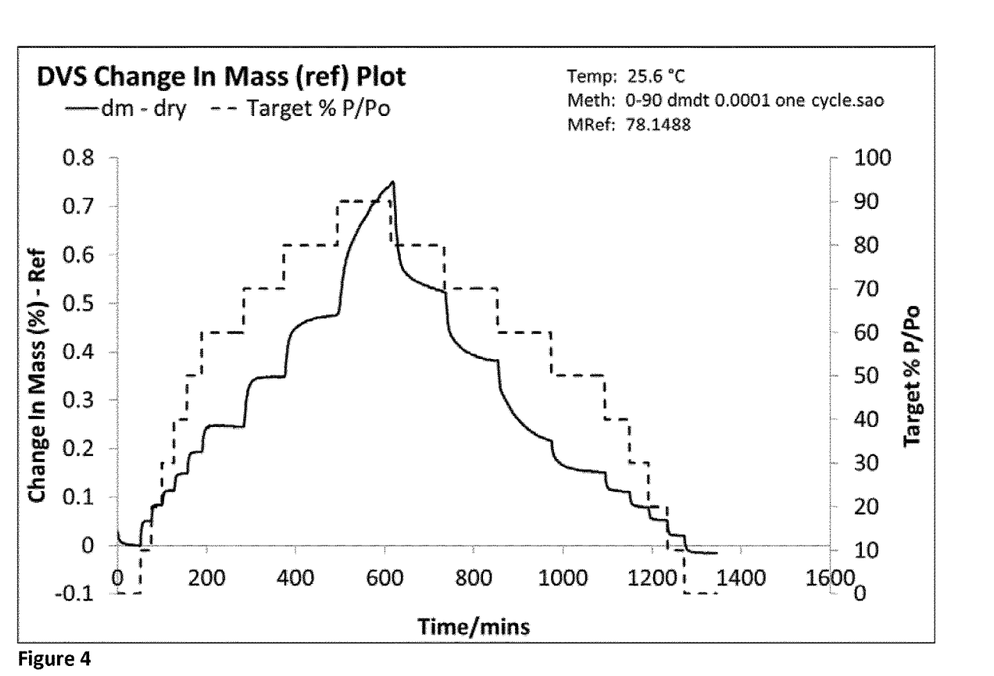
FIG. 4 shows the DVS trace for co-jet milled glycopyrrolate and magnesium stearate (1% w/w) using a milling gas having humidity 25% RH and the analysed by DVS immediately after micronisation (Example 1).

Samples of the freshly micronized composite glycopyrrolate particles were immediately analysed using DVS (FIG. 4), wet particle size analysis.

Example 2: Co-Jet Milled Glycopyrrolate and Magnesium Stearate (0.5% w/w) in Humidified Gas (25% RH) Using Liquid Aerosol Unmicronised glycopyrrolate ($D_{10}$=2.89 µm, $D_{50}$=16.0 µm, $D_{90}$=49.0 µm determined by Malvern Mastersizer 3000 wet analysis method) was pre-stirred with magnesium stearate ($D_{10}$=2.8 µm, $D_{50}$=8.8 µm, $D_{90}$=27.4 µm determined by Malvern Mastersizer 3000 wet analysis method) in a glass beaker using a metal spatula for 30 seconds before micronization in an AS-50 spiral jet mill (Inlet pressure=5 Bar, Grinding Pressure=3 Bar, Averaged Feed Rate=2 g/min).

The Formulation was produced by using a milling gas at elevated humidity (23.5-24.9% RH and at 17.3-18.3° C.) using liquid aerosol. The outlet of an ultrasonic wave nebuliser was connected to the grinding chamber of an AS-50 jet mill via tube piping ensuring that water did not drip into the grinding chamber and that nebulised water aerosol combined with the unmicronised glycopyrrolate and magnesium stearate. The humidities were measured prior to jet milling by placing a portable hygrometer with the probe in the exiting gas stream at the outlet of the collection vessel.

Figure 5:
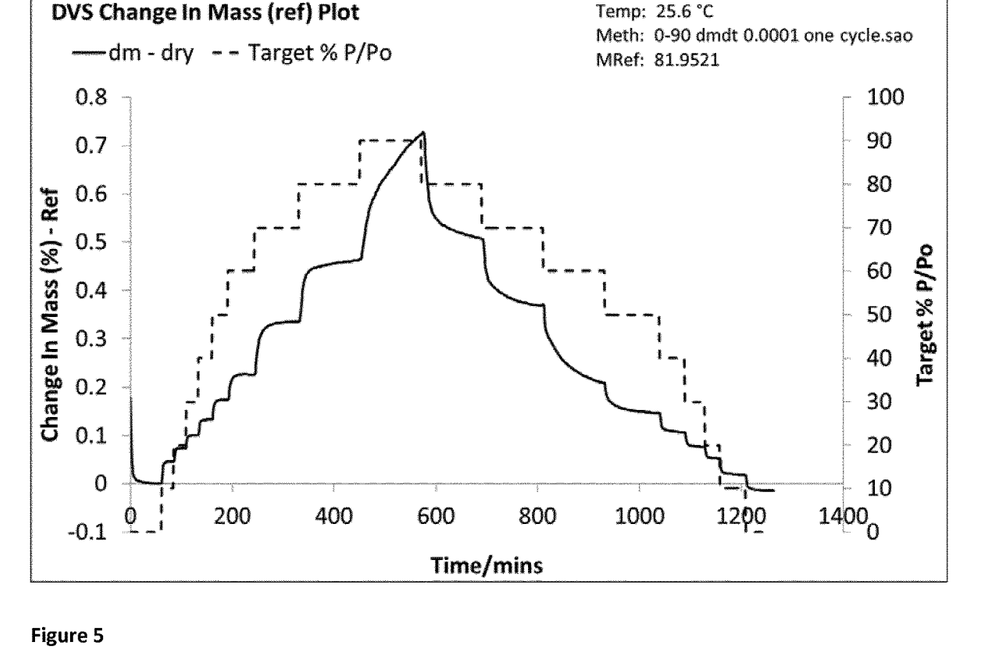
FIG. 5 shows the DVS trace for co-jet milled glycopyrrolate and magnesium stearate (0.5% w/w) using a milling gas having humidity 25% RH and the analysed by DVS immediately after micronisation (Example 2).

Samples of the freshly micronized composite glycopyrrolate particles were immediately analysed using DVS (FIG. 5), wet particle size analysis.

Example 3: Co-Jet Milled Glycopyrrolate and Magnesium Stearate (0.25% w/w) in Humidified Gas (10% RH) Using Liquid Aerosol Unmicronised glycopyrrolate ($D_{10}$=2.89 µm, $D_{50}$=16.0 µm, $D_{90}$=49.0 µm determined by Malvern Mastersizer 3000 wet analysis method) was pre-stirred with magnesium stearate ($D_{10}$=2.8 µm, $D_{50}$=8.8 µm, $D_{90}$=27.4 µm determined by Malvern Mastersizer 3000 wet analysis method) in a glass beaker using a metal spatula for 30 seconds before micronization in an AS-50 spiral jet mill (Inlet pressure=5 Bar, Grinding Pressure=3 Bar, Averaged Feed Rate=2 g/min).

The Formulation was produced by using a milling gas at elevated humidity (6.9-8.8% RH and at 18.0-18.1° C.) using liquid aerosol. The outlet of an ultrasonic wave nebuliser was connected to the grinding chamber of an AS-50 jet mill via tube piping ensuring that water did not drip into the grinding chamber and that nebulised water aerosol combined with the unmicronised glycopyrrolate and magnesium stearate. The humidities were measured prior to jet milling by placing a portable hygrometer with the probe in the exiting gas stream at the outlet of the collection vessel.

Figure 6:
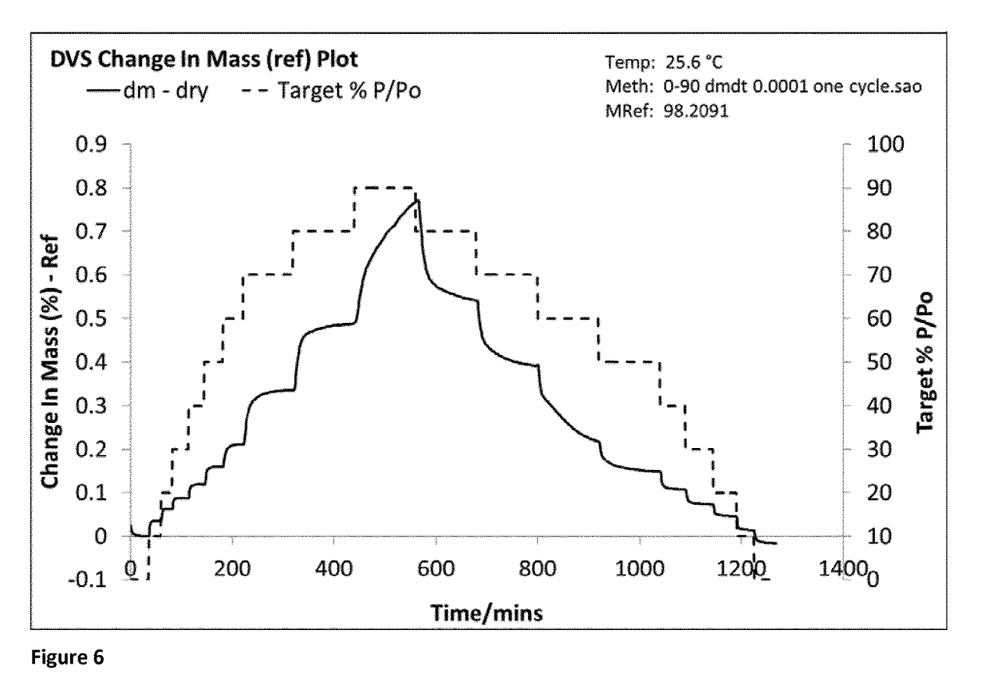
FIG. 6 shows the DVS trace for co-jet milled glycopyrrolate and magnesium stearate (0.25% w/w) using a milling gas having humidity 10% RH and the analysed by DVS immediately after micronisation (Example 3).

Samples of the freshly micronized composite glycopyrrolate particles were immediately analysed using DVS (FIG. 6), wet particle size analysis.

Example 4: Co-Jet Milled Glycopyrrolate and Magnesium Stearate (1% w/w) in Humidified Gas (10% RH) Using Liquid Aerosol Unmicronised glycopyrrolate (14.25 g, $D_{10}$=2.89 µm, $D_{50}$=16.0 µm, $D_{90}$=49.0 µm determined by Malvern Mastersizer 3000 wet analysis method) was pre-stirred with magnesium stearate (0.75 g, $D_{10}$=2.8 µm, $D_{50}$=8.8 µm, $D_{90}$=27.4 µm determined by Malvern Mastersizer 3000 wet analysis method) in a glass beaker using a metal spatula for 30 seconds before micronization in an AS-50 spiral jet mill (Inlet pressure=5 Bar, Grinding Pressure=3 Bar, Averaged Feed Rate=2 g/min).

The Formulation was produced by using a milling gas at elevated humidity (6.3-8.3% RH and at 18.2-18.4° C.) using liquid aerosol. The outlet of an ultrasonic wave nebuliser was connected to the grinding chamber of an AS-50 jet mill via tube piping ensuring that water did not drip into the grinding chamber and that nebulised water aerosol combined with the unmicronised glycopyrrolate and magnesium stearate. The humidities were measured prior to jet milling by placing a portable hygrometer with the probe in the exiting gas stream at the outlet of the collection vessel.

Figure 7:
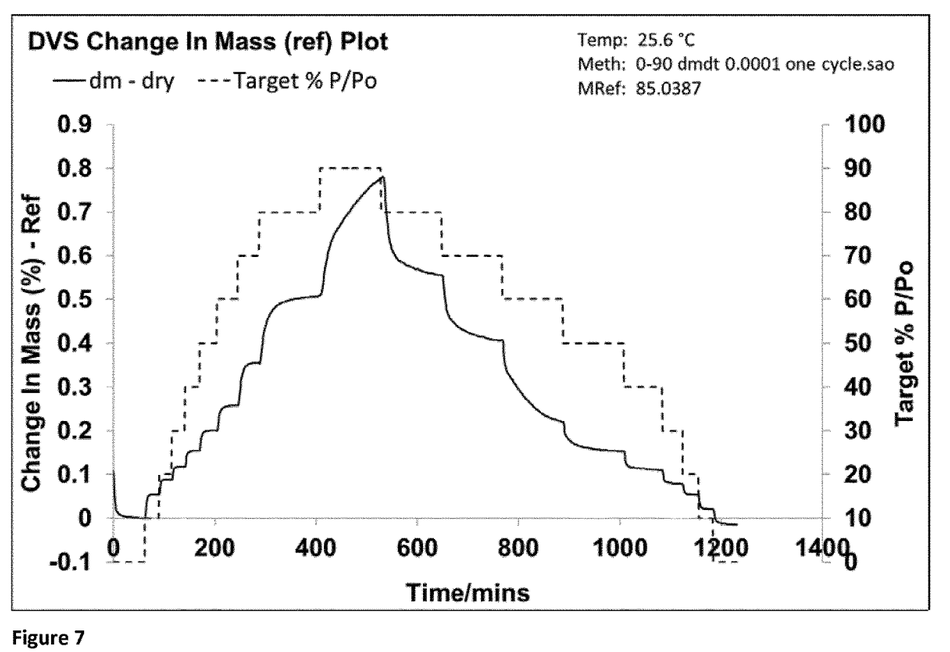
FIG. 7 shows the DVS trace for co-jet milled glycopyrrolate and magnesium stearate (1% w/w) using a milling gas having humidity 10% RH and the analysed by DVS immediately after micronisation (Example 4).
Figure 8:
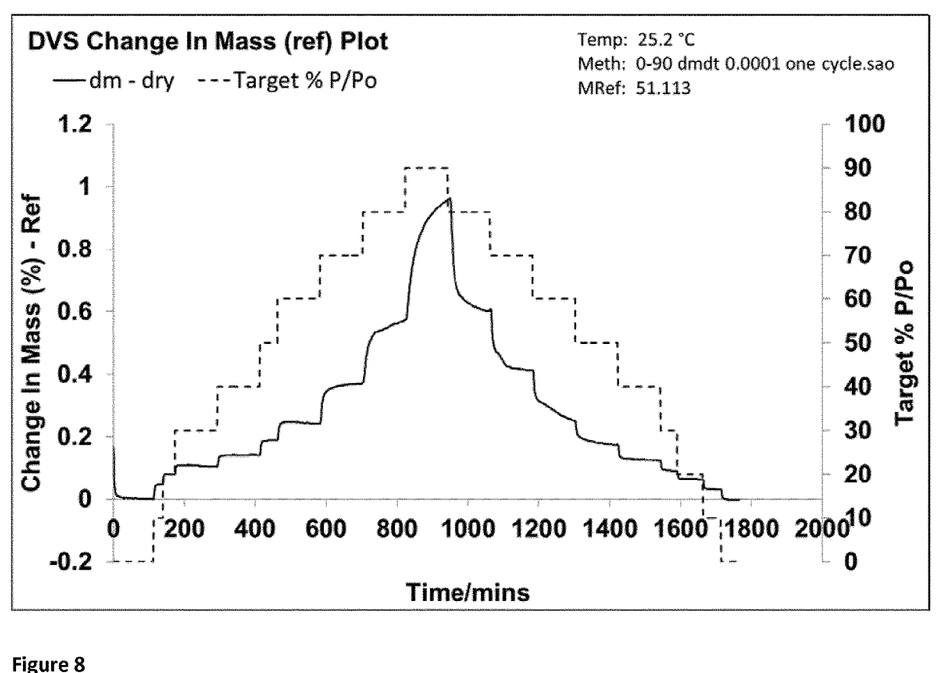
FIG. 8 shows the DVS trace for co-jet milled glycopyrrolate and magnesium stearate (1% w/w) using a milling gas having humidity 5% RH and the analysed by DVS immediately after micronisation (Example 5).

Samples of the freshly micronized composite glycopyrrolate particles were immediately analysed using DVS (FIG. 7), wet particle size analysis.

Example 5: Co-Jet Milled Glycopyrrolate and Magnesium Stearate (1% w/w) in Humidified Gas (5% RH) Using Liquid Aerosol A different batch of unmicronised glycopyrrolate ($D_{10}$=1.09 µm, $D_{50}$=2.90 µm, $D_{90}$=10.4 µm determined by Malvern Mastersizer 3000 wet analysis method) was pre-stirred with magnesium stearate ($D_{10}$=2.06 µm, $D_{50}$=6.57 µm, $D_{90}$=19.9 µm determined by Malvern Mastersizer 3000 wet analysis method) in a glass beaker using a metal spatula for 30 seconds before micronization in an AS-50 spiral jet mill (Inlet pressure=5 Bar, Grinding Pressure=3 Bar, Averaged Feed Rate=2 g/min).

The Formulation was produced by using a milling gas at elevated humidity (5.5-6.6% RH and at 18.2° C.) using liquid aerosol. The outlet of an ultrasonic wave nebuliser was connected to the grinding chamber of an AS-50 jet mill via tube piping ensuring that water did not drip into the grinding chamber and that nebulised water aerosol combined with the unmicronised glycopyrrolate and magnesium stearate. The humidities were measured prior to jet milling by placing a portable hygrometer with the probe in the exiting gas stream at the outlet of the collection vessel.

Samples of the freshly micronized composite glycopyrrolate particles were immediately analysed using DVS (FIG. 8), wet particle size analysis.

Results: Examples 1-5

TABLE 1

Particle size (μm) distributions wet analysis using the Malvern Mastersizer and Dynamic Vapour Sorption for Formulations produced in Example 1-5.

| | Example | | |
|---|---|---|---|
| | $D_{10}$ | $D_{50}$ | $D_{90}$ |
| Unmicronised glycopyrrolate | 2.89 | 16.0 | 49.0 |
| $1_{(t=0)}$ | 0.822 | 2.05 | 3.85 |
| $1_{(t=0,\ DVS)}$ | | No amorphous material detected (see FIG. 4) | |
| $1_{(t=24\ hrs)}$ | 0.988 | 2.48 | 4.89 |
| $1_{(t=1\ week)}$ | 0.989 | 2.49 | 4.86 |
| $1_{(t=3\ week)}$ | 1.00 | 2.54 | 4.99 |
| $2_{(t=0)}$ | 0.952 | 2.35 | 4.52 |
| $2_{(t=0,\ DVS)}$ | | No amorphous material detected (see FIG. 5) | |
| $2_{(t=3\ days)}$ | 1.00 | 2.50 | 4.80 |
| $2_{(t=1\ week)}$ | 1.03 | 2.70 | 5.57 |
| $2_{(t=3\ week)}$ | 1.11 | 2.88 | 5.81 |
| $3_{(t=0)}$ | 0.978 | 2.48 | 5.27 |
| $3_{(t=0,\ DVS)}$ | | No amorphous material detected (see FIG. 6) | |
| $3_{(t=24\ hrs)}$ | 1.01 | 2.69 | 8.38 |
| $3_{(t=1\ week)}$ | 1.02 | 2.77 | 7.89 |
| $3_{(t=3\ week)}$ | 1.10 | 2.94 | 11.3 |
| $4_{(t=0)}$ | 0.806 | 1.96 | 3.68 |
| $4_{(t=0,\ DVS)}$ | | No amorphous material detected (see FIG. 7) | |
| $4_{(t=24\ hrs)}$ | 0.921 | 2.30 | 4.55 |
| $4_{(t=1\ week)}$ | 0.978 | 2.41 | 4.77 |
| $4_{(t=3\ week)}$ | 1.06 | 2.80 | 6.58 |
| $5_{(t=0)}$ | 0.861 | 1.89 | 3.50 |
| $5_{(t=0,\ DVS)}$ | | No amorphous material detected (see FIG. 8) | |
| $5_{(t=24\ hrs)}$ | 0.904 | 2.12 | 4.27 |
| $5_{(t=1\ week)}$ | 0.938 | 2.28 | 4.58 |

Discussion: Examples 1-5

When milled under dry conditions, freshly jet milled glycopyrrolate contains substantial amounts of amorphous material as confirmed by the DVS data (See FIG. 3). The presence of this amorphous material in the company of moisture, if not controlled correctly, leads to the formation of large agglomerates in an unpredictable fashion.

When jet milled with liquid aerosol in the grinding chamber, freshly co-jet milled glycopyrrolate formulations contain no amorphous material (Formulations 1-5 | FIGS. 4-8). The DVS trace demonstrates that no amorphous material was present in this freshly micronized glycopyrrolate (t=0). Without this amorphous material on the surface of micronized glycopyrrolate, the primary particles remain small, physically stable and respirable after 3 weeks (see Table 1).

The invention claimed is:

1. A method for making a dry powder formulation, comprising:

co-jet milling particles of glycopyrrolate and magnesium stearate in a jet mill comprising a grinding chamber to produce a dry powder formulation comprising physically stable micronized composite particles, wherein the glycopyrrolate is present in an amount from 50% (w/w) to 99.9% (w/w) of the particles of glycopyrrolate and magnesium stearate, wherein the magnesium stearate is present in an amount of from 0.1% (w/w) to 50% (w/w) of the particles of glycopyrrolate and magnesium stearate, wherein the jet milling is performed using a milling gas, wherein an humidity in the grinding chamber during the co-jet milling is between 5% and 29% Relative Humidity (RH), and wherein no separate step of conditioning the dry powder formulation is performed.

2. The method of claim 1, wherein the dry powder formulation further comprises particles of an excipient carrier.

3. The method of claim 2, wherein the excipient carrier is lactose.

4. The method of claim 2, wherein the excipient carrier is alpha-lactose monohydrate.

5. The method of claim 2, wherein the excipient carrier is anhydrous lactose.

6. The method of claim 1, wherein the glycopyrrolate is present in an amount from 55% (w/w) to 99.9% (w/w) of the combined glycopyrrolate and magnesium stearate and the magnesium stearate is present in an amount from 0.1% (w/w) to 45% (w/w) of the combined glycopyrrolate and magnesium stearate.

7. The method of claim 1, wherein the humidity in the grinding chamber during the co-jet milling is supplied by a humidifier configured to supply moisture to the grinding chamber of the jet mill.

8. The method of claim 1, wherein the humidity in the grinding chamber is supplied by an aerosol generator configured to supply liquid aerosol to the grinding chamber of the jet mill.

9. The method of claim 8, wherein the aerosol generator is positioned externally to the grinding chamber of the jet mill, and wherein the aerosol generator further comprises a port configured to supply a liquid aerosol into the grinding chamber of the jet mill.

10. The method of claim 9, wherein the port is further configured to simultaneously supply the particles of glycopyrrolate and magnesium stearate and the liquid aerosol as a feed stock into the grinding chamber.

11. The method of claim 9, wherein the port is further configured to simultaneously supply the particles of glycopyrrolate and magnesium stearate and the liquid aerosol as a feed stock into the grinding chamber, and wherein the particles of glycopyrrolate and magnesium stearate are co-located.

12. The method of claim 8, wherein the liquid aerosol has a $D_{90}$ less than 100 μm as measured by laser diffraction.

13. The method of claim 8, wherein the liquid aerosol has a $D_{90}$ less than 50 μm as measured by laser diffraction.

14. The method of claim 8, wherein the liquid aerosol has a $D_{90}$ less than 20 μm as measured by laser diffraction.

15. The method of claim 1, wherein the humidity in the grinding chamber during co-jet milling is from 10% to 29% RH.

16. The method of claim 1, wherein the humidity in the grinding chamber during the co-jet milling is from 15% to 29% RH.

17. The method of claim 1, wherein the humidity in the grinding chamber during the co-jet milling is from 21% to 29% RH.

18. The method of claim 1, further comprising combining indacaterol maleate and the dry powder formulation.

19. The method of claim 1, further comprising combining indacaterol maleate, mometasone furoate and the dry powder formulation.

* * * * *